United States Patent [19]

Wilbur et al.

[11] Patent Number: 5,057,301

[45] Date of Patent: Oct. 15, 1991

[54] MODIFIED CELLULAR SUBSTRATES USED AS LINKERS FOR INCREASED CELL RETENTION OF DIAGNOSTIC AND THERAPEUTIC AGENTS

[75] Inventors: Daniel S. Wilbur, Edmonds; Mark D. Hylarides, Everett, both of Wash.

[73] Assignee: NeoRx Corporation, Seattle, Wash.

[21] Appl. No.: 178,418

[22] Filed: Apr. 6, 1988

[51] Int. Cl.$^5$ .................. A61K 39/395; A61K 37/10; A61K 43/00; C07H 15/00

[52] U.S. Cl. .................................... 424/1.1; 424/85.91; 536/18.4; 514/8; 530/389; 530/395; 530/399; 530/390; 530/391

[58] Field of Search ................ 424/1.1, 85.91; 534/10, 534/14; 530/395, 388, 389, 390; 536/18.4; 514/8

[56] References Cited

U.S. PATENT DOCUMENTS

| | | | |
|---|---|---|---|
| 3,817,978 | 6/1974 | Jenkins et al. | 536/18.4 X |
| 3,852,413 | 12/1974 | Cammarata | 424/1.1 |
| 4,126,669 | 11/1978 | Rothman et al. | 424/1.1 |
| 4,202,874 | 5/1980 | Akerkar et al. | |
| 4,269,826 | 5/1981 | Zimmermann et al. | |
| 4,275,000 | 6/1981 | Ross | |
| 4,301,140 | 11/1981 | Frank et al. | 424/1.1 |
| 4,308,050 | 12/1981 | Felix | |
| 4,331,590 | 5/1982 | Bocuslaski et al. | |
| 4,356,170 | 10/1982 | Jennings et al. | |
| 4,385,046 | 5/1983 | Milbrath et al. | 424/1.1 |
| 4,399,817 | 8/1983 | Benedict | |
| 4,474,746 | 10/1984 | Blau et al. | |
| 4,507,234 | 3/1985 | Kato et al. | |
| 4,524,059 | 6/1985 | Elmaleh et al. | |
| 4,569,789 | 2/1986 | Blattler et al. | |
| 4,585,754 | 4/1986 | Meisner et al. | |
| 4,671,958 | 6/1987 | Rodwell et al. | |
| 4,692,434 | 9/1987 | Hertel | 536/18.4 X |
| 4,709,016 | 11/1987 | Giese | |
| 4,722,906 | 2/1988 | Guire | |
| 4,732,864 | 3/1988 | Tolman | |
| 4,741,900 | 5/1988 | Alvarez et al. | |
| 4,746,505 | 5/1988 | Jones et al. | |
| 4,771,127 | 9/1988 | Cryz et al. | 530/395 |
| 4,793,986 | 12/1988 | Serino et al. | 424/1.1 |
| 4,859,449 | 8/1989 | Mattes | 530/395 |

FOREIGN PATENT DOCUMENTS

| | | |
|---|---|---|
| 094844 | 11/1983 | European Pat. Off. |
| 289187 | 11/1988 | European Pat. Off. |
| 336364 | 10/1989 | European Pat. Off. |

OTHER PUBLICATIONS

European Search Report for Application No. EP/89105876.

Goodman et al., "New Myocardial Imaging Agents: Preparation of 15-(p-[$^{123}$I]-Iodophenyl)-7-Tellurapontadecanoic Acid from Na[$^{123}$I] by a Triazene Decomposition Reaction", in Paras and Thiessen (eds.), *The Developing Role of Short-Lived Radio-nuclides in Nuclear Medical Practice*, Office of Science and Technical Information, U.S. Dept. of Energy, 1985 [Goodman et al., I].

Liefhold et al., "Synthesis, Labeling, and Pharmacokinetics of $^{131}$I Labeled Phenylene-Iodophenyl-Fatty Acids (PHIPA)", in *Sixth Int. Symposium on Radiopharmaceutical Chemistry*, pp. 212–14, 1986.

Knapp, Jr. et al., "Development of Radioiodinated Fatty Acids for Applications in Nuclear Cardiology", in Paras and Thiessen (eds.), *The Developing Role of Short-Lived Radionuclides in Nuclear Medical Practice*, (List continued on next page.)

*Primary Examiner*—John S. Maples
*Attorney, Agent, or Firm*—Kathryn A. Seese

[57] ABSTRACT

Modified cellular substrates are used as linking groups that are recognized as cellular substrates by intracellular metabolic enzymes. The linking groups function to attach a ligand, such as a drug or radionuclide, to a targeting protein, such as an antibody or antibody fragment. The false substrate structure of the linking groups causes increased cellular retention of the linking group/ligand conjugate because the enzymes used for catabolism of the substrate are inhibited by the false substrate structure of the linking group.

12 Claims, 4 Drawing Sheets

OTHER PUBLICATIONS

Office of Science and Technical Information, U.S. Dept. of Energy, [Knapp, Jr. et al. I].

Gallagher et al., "Radiopharmaceuticals XXVII. 18F–Labeled 2–Deoxy-2–Fluoro-D–Glucose as a Radiopharmaceutical for Measuring Regional Myocardial glucose Metabolism in Vivo: Tissue Distribution and Imaging Studies in Animals", *J. Nucl. Med.* 18:990–996, 1977 [Gallagher et al., I].

Knapp, Jr. et al., "Effect of Tellurium Position on the Myocardial Uptake of Radioiodinated 18–Iodotellura-17–Octadecanoic Acid Analogues", *J. Med. Chem.* 27:57–63, 1984, [Knapp, Jr. et al., II].

Livni et al., "Beta-methyl[1–11C] heptadecanoic Acid: A New Myocardial Metabolic Tracer for Position Emission Tomography", *J. Nucl. Med.* 23:169–175, 1982.

Elmaleh et al., "Myocardial Imaging with 9–[Te–123m-]Telluraheptadecanoic Acid", *J. Nucl. Med.* 22:994–999, 1981 [Elmleh et al. 1].

Goodman et al., "Synthesis and Evaluation of Radioiodinated Terminal p–Iodophenyl–Substituted α–and β–Methyl–Branched Fatty Aciods", *J. Med. Chem.* 27:340–397, 1984 [Goodman et al. II].

Goodman et al., "New Myocardial Imaging Agents: Synthesis of 15–(p–Iodophenyl)-3(R,S)–methylpentadecanoic Acid by Decomposition of a 3,3–(1,5–Pentarediyl)triazene Precursor", *J. Org. Chem.* 49:2322–2325, 1984 [Goodman et al. III].

Gallagher et al., "Metabolic Trapping as a Principle of Radio-pharmaceutical Design: Some Factors Responsible for the Biodistribution of [18F]2–Deoxy-2–Fluoro-D–Glucose", *J. Nucl. Med.* 19:1154–1161, 1978 [Gallagher et al. II].

Elmaleh et al., "Comparison of 11C and 14C-Labeled Fatty Acids and Their β-Methyl Analogs", *Int. J. Med. Biol.* 10:181–187, 1983 [Elmaleh et al. II].

Pande et al., "Inhibition of Long-Chain Fatty Acid Activation by α-Bromopalmitate and Phytanate", *Biochim. Biophys. Acta.* 248:156–166, 1971.

Goodman et al., "Synthesis and Biological Evaluation of 17–[131I]Iodo-9–Telluraheptadecanoic Acid, a Potential Myocardial Imaging Agent", *J. Med. Chem.* 25:613–618, 1982[Goodman et al. IV].

Goodman et al., "A New, Well-Retained Myocardial Imaging Agent: Radioiodinated 15–(p–Iodophenyl)-6–Tollurapntadecanoic Acid", *J. Nucl. Med.* 23:904–908, 1982 [Goodman et al. V].

Knapp, Jr. et al., "New Myocardial Imaging Agents: Stabilization of Radioiodine as a Terminal Vinyl Iodide Moiety on Tellurium Fatty Acids", *J. Med. Chem.* 26:1293–300, 1983 [Knapp, Jr. et al. III].

Otto et al., "Radioiodinated Branched-Chain Fatty Acids: Substrates for Beta Oxidation? Concise Communication", *J. Nucl. Med.* 25:75–80, 1985.

Knapp, Jr. et al., "Effects of Chain Length and Tellurium Position on the Myocardial Uptake of Te–123m Fatty Acids", *J. Nucl. Med.* 22:988–993, 1981 [Knapp, Jr. et al. IV].

Pittman et al., (J. Biol. Chem., vol. 254, No. 15, Aug. 10, 1979, pp. 6876–6879).

Pittman et al., (Biochem J., vol. 212, pp. 791–800 [1983]).

1  R = H
2  R = Protecting Group

3  R = Protecting Group

4  R = Protecting Group
5  R = H

6

11

12

13

14

15

16

MODIFIED CELLULAR SUBSTRATES USED AS LINKERS FOR INCREASED CELL RETENTION OF DIAGNOSTIC AND THERAPEUTIC AGENTS

TECHNICAL FIELD

This invention relates to protein conjugates containing groups that are (1) recognized by cells as substrates; (2) taken up intracellularly; (3) retained within the cell for an increased length of time; and (4) not metabolized within the cells because of their chemical structure. The linkage groups join diagnostic or therapeutic agents, such as cytotoxic molecules and/or radionuclides, to targeting proteins such as antibodies and antibody fragments.

BACKGROUND OF THE INVENTION

The use of monoclonal antibodies to target chemotherapeutic agents and/or radionuclides has been considered a "magic bullet" approach for treatment of cancer. This "magic bullet" approach to cancer therapy has been examined in many forms for many years. The present use of the basic concept of the "magic bullet" includes linking a cancer cell-specific antibody to a chemotherapeutic agent or radionuclide such that the antibody will target the cancer cell, thereby exposing the cancer cells to a therapeutic agent or a radionuclide for detection or treatment of the cancer.

Some compelling data that suggests the "magic bullet" approach might work are given in the following points. Antibody drug conjugates have been shown to deliver up to 1,000 fold more drug to the tumor cells when conjugated to an antigen-specific monoclonal antibody than is possible by diffusion of free drug. Additionally, antibody-drug conjugates have shown increased response rates and drug effectiveness. They have also shown ability to overcome drug resistance which has occurred from treatment with non-antibody-bound therapeutic drugs. Other examples include specific localization of radionuclides where labeled antibody fragments have been found to obtain tumor to non-tumor tissue ratios of over 80:1.

While specific delivery of radionuclides and other cytotoxic agents has been demonstrated, the retention of the radionuclide at the tumor site and intracellular uptake of the radionuclide is often very poor. One method of release of the chemotherapeutic agent is through the intracellular internalization and metabolism of the antibody or intracellular degradation of the linkage between the antibody and the agent. This process may release the chemotherapeutic agent or radionuclide intracellularly. However, the intracellular release of radionuclides being used for diagnosis or therapy of cancers may allow the free radionuclide to diffuse out from the target cell prior to the radioactive decay. Likewise, certain drugs and other relatively small molecules released inside a target cell may diffuse out of the cell.

The diagnostic or cytotoxic effect of radionuclides is a non-specific cellular interaction which is reliant upon the amount of radioactivity delivered to the tumor tissue versus other tissues. Thus the initial specific delivery of a radionuclide by antibody conjugates does not assure that a diagnostic imaging or therapeutic effect can be obtained if that radioactivity does not remain in the tumor tissue. Accordingly, there is a need in the art for protein conjugates that have a means to enhance cellular retention of the diagnostic or therapeutic component to increase imaging contrast and therapeutic potency.

SUMMARY OF THE INVENTION

The present invention provides conjugates of the formula:

Y—Linker—Ligand wherein:
Y is a targeting protein or a protein conjugation group;
the linker is a chemically modified cellular substrate bonded to Y; and
the ligand is a ligand comprising a diagnostic or therapeutic agent, or a ligand precursor, and is bonded to the linker.

The conjugate comprises a targeting protein such as an antibody, an antibody fragment, a hormone, or a serum protein; or a protein conjugation group that is reactive with a targeting protein. The conjugate also comprises a linking group comprising a chemically modified cellular substrate, which is bonded to Y; and a ligand attached to said linking group. The ligand comprises a diagnostically or therapeutically effective agent. The ligand may comprise diagnostic or therapeutic radionuclides (within a chelate or otherwise chemically bonded to a small molecule), other therapeutic agents such as cytotoxic drugs, or other diagnostic imaging agents, such as electron-dense chemicals. Preferably, the ligand contains a radionuclide. The conjugate may comprise more than one ligand. The ligand-modified cellular substrate linker conjugates comprising protein conjugation groups are reacted with targeting proteins to bind the ligand to the protein through the linker.

Based upon immune selection or pharmacologic receptor recognition, the targeting protein targets or directs the conjugate to a desired target cell, tissue or body site in vivo. The ligand contains the active cytotoxic or imaging moiety that can have therapeutic or diagnostic uses. The linker is a modified cellular substrate that is able to be retained within the cell due to inhibition of cellular metabolism of the linking group. Therefore, the targeting protein-linker-ligand conjugate functions to specifically target desired target cells and enhance cellular uptake and retention of the active ligand moiety in the cells. Preferred linkers are modified sugars, modified fatty acids, and other cellular energy sources.

The present invention also provides a method for increasing the retention of a ligand comprising a diagnostic or therapeutic agent in target cells within a human or mammalian host, comprising administering to the host a protein conjugate comprising the ligand bound to a targeting protein through a chemically modified cellular substrate linker.

DETAILED DESCRIPTION OF THE INVENTION

Figure 1:
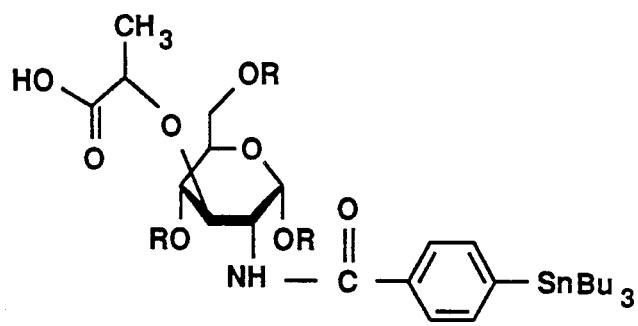
FIG. 1 depicts the intermediate compounds (1-6) in the synthesis of a protein conjugate of the invention comprising a modified sugar linker.
Figure 1:
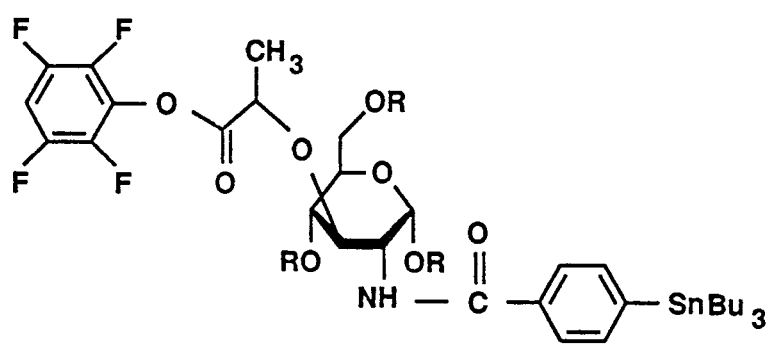
Figure 1:
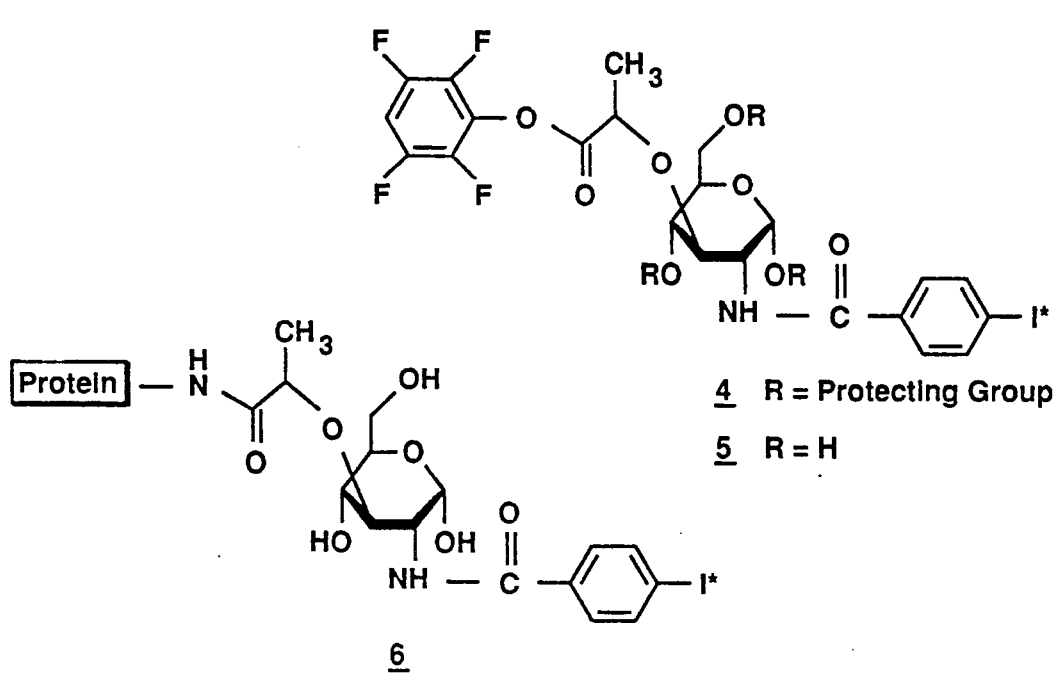

The present invention comprises ligand-linker conjugates, wherein the linker is a chemically modified cellular substrate having a protein conjugation group attached thereto, and protein conjugates prepared therefrom. The protein conjugate comprises a targeting protein that delivers the protein conjugate to a specific cellular or tissue target site when administered in vivo. The targeting is preferably accomplished by immune selectivity through antigen/antibody interactions. The targeting protein is bound to a chemically modified cellular substrate (including biochemically modified cellular substrates), or naturally occurring compound which mimics a cellular substrate, that functions as a linking group within the conjugate.

Suitable targeting proteins include, but are not limited to, serum proteins, hormones, and antibodies, preferably monoclonal antibodies. The antibodies employed in the present invention may be intact antibody molecules, fragments thereof, or functional equivalents thereof, including genetically engineered variations thereof. Examples of antibody fragments are $F(ab')_2$, Fab', Fab, and Fv fragments, which may be produced by conventional procedures. While polyclonal antibodies may be employed in the present invention, monoclonal antibodies (MAbs) are preferred. In one embodiment of the invention, the target cells are cancer cells, and the MAbs are directed against a tumor-associated antigen in humans. Many monoclonal antibodies directed against specific target sites (e.g., cancer cells) in vivo have been developed. Examples of such MAbs are anti-TAC, or other interleukin-2 receptor antibodies; 9.2.27 and NR-ML-05 to a 250 kilodalton human melanoma associated proteoglycan; NR-LU-10 to 37–40 kilodalton pancarcinoma glycoprotein; and OVB3 to an as yet unidentified cancer-associated antigen.

The protein conjugation group attached to the modified substrate linker is a functional group which will react with a group on a targeting protein, thereby forming a bond between the linker and the protein. Suitable protein conjugation groups include but are not limited to, active esters (including carboxylic esters, imide esters, succinimidyl esters, phenolic esters, and imidate esters), primary or secondary amines, hydrazides, hydrazines, carboxylate, isothiocyanates, isocyanates, Michael-type acceptor groups such as maleimides, thiols, anhydrides, and alkyl halides.

The chemically modified cellular substrate linking group can be, for example, a modified monosaccharide, modified polysaccharide; modified fatty acid, or a modified biochemical energy source. Preferably, the modified monosaccharide is a halogenated analog of a naturally occurring sugar substrate, e.g., a halogenated-deoxyglucose derivative, or is a carbocyclic analog of a sugar such as ribose. Preferably, the halo group in the halogenated derivatives is a fluorine. Examples of modified polysaccharides are dimers, trimers, or polymers in the range of 2-10 saccharide units and containing one or more halogenated or carbocyclic sugar analogs, e.g., halogenated-deoxyglucose derivatives or carbocyclic analogs of ribose. Certain naturally occurring sugar analogs may be considered "modified cellular substrates" and include monosaccharides, disaccharides, or polysaccharides. Most preferably the naturally occurring sugar analogs are monosaccharides and disaccharides which are amino sugars. Some naturally occurring sugars of interest are constituents of biomembranes such as cell walls and umbilical cords (e.g., muramic acid and hyalobiuronic acid).

The modified fatty acids generally are single-chain fatty acids of from about 6 to 30 methylene groups, preferably from about 8 to 25 methylene groups and most preferably from 12 to 20 total carbon atoms. The modified fatty acids may be either saturated or unsaturated. A modification of a fatty acid can be carried out, for example, by attaching a metal group either within the chain or branched to a carbon atom on the chain. Preferably, a metal group is inserted within the chain of the fatty acid.

In one embodiment of the invention, the modified fatty acid is of the formula:

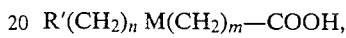

$R'(CH_2)_n M(CH_2)_m$—COOH, wherein M is a metal group, and n and m are integers between 1 and 20, with the proviso that the sum of n plus m does not exceed 30. R' represents a group that will react with a desired ligand to bind the ligand to the metal-containing fatty acid. Chemical reaction procedures which may be used to bind ligands to such modified cellular substrates are discussed below. Alternatively, R' may represent a precursor of a ligand. The ligand precursor may be a molecule to which a radionuclide will be bound to form the ligand. Examples of such precursors are chelating compounds or molecules containing a phenyl ring, wherein a radiohalogen will be attached to the phenyl ring. The modified fatty acid and the ligand precursor R' may be synthesized as a single molecule, as illustrated in the examples below, wherein the ligand precursor comprises a phenyl ring having a tri-alkyl stannane attached thereto in the para position.

The terminal carboxylic acid group in the above formula is a protein conjugation group, or may be derivatized to generate other protein conjugation groups. The carboxylate group may be reacted with a free amine group on a protein by using a water soluble carbodiimide coupling agent. Alternatively, other protein conjugation groups (e.g., esters, anhydrides, acyl-succinimides, and maleimides) may be produced from the —COOH precursor using conventional chemical reaction procedures.

The metal group may comprise any metal atom which can form two or more covalent bonds to carbon atoms. Examples of appropriate metal atoms are arsenic, mercury, tellurium, selenium, and silicon. The silicon group may contain two R groups attached according to the following formula:

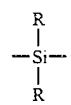

wherein R is an alkyl group having between 1 and 6 carbon atoms and preferably, R is an alkyl group between 1 and 4 carbon atoms. Most preferably, the R group attached to the silicon moiety is a methyl group.

In other embodiments of the invention, a modification of the fatty acid involves attaching an alkyl or phenyl group (generally one or two of such groups) as a branch group to a carbon atom on the chain of the fatty acid. The alkyl group may be a methyl group, for example. Alternatively, a phenyl group may be inserted within the carbon chain of the fatty acid.

The ligand or ligand precursor is also bound to the linker. The ligand is a diagnostically or therapeutically effective agent including, but not limited to, a compound containing a radionuclide, a therapeutic agent such as a cytotoxic drug, or a diagnostic imaging agent, such as an electron-dense chemical (useful for nuclear magnetic resonance imaging or x-ray contrast). Preferably, the ligand is a radionuclide that is bound by a sigma bond or is within a chelating moiety. Radionuclides suitable for use as ligands are well known to those skilled in this art and may be any radionuclide known to be useful for diagnostic or therapeutic purposes. Examples of appropriate radionuclides include Y-90, Cu-67, Ga-67, Ga-68, Zr-89, Tc-99m, In-111, I-123, I-125, I-131, Br-75, Br-76, Au-198, Au-199, Br-77, F-18, Rh-105, Re-188, Re-186, At-211, Pb-203 and Pb-212.

The radionuclides may be in the form of a stable complex, e.g., in the form of a chelate or bound to another type of small molecule. Thus, the ligand may comprise any of a number of chelating compounds or other small molecules capable of binding radionuclides. Such chelating compounds include the diamide dimercaptide ($N_2S_2$) compounds described in European patent application publication number 188,256. European patent application publication number 173,424 describes "$N_3S$" and "$N_4$" chelating compounds. These chelators, which comprise sulfur and/or nitrogen donor atoms are useful for the preparation of chelates of radionuclide metals such as $^{99m}Tc$, $^{186}Re$, and $^{188}Re$. Another known chelating compound is diethylenetriaminepentaacetic acid (DTPA), described by Fritzberg (*J. Nuc. Med. Tech.* Vol. 12, No. 4, December 1984) and in U.S. Pat. No. 4,652,440. Other radionuclide metal chelate compounds are described in U.S. Pat. Nos. 4,287,362; 4,421,735; and 4,678,667.

The preparation of radiolabeled vinyl-iodo derivative compounds is described in co-pending U.S. patent application Ser. No. 039,155. Small molecules that bind radiohalogens (e.g., $^{123}I$, $^{125}I$, $^{131}I$, $^{211}At$, etc.) are described in European Patent application publication number 203,764. Ligands such as $^{131}I$-para-iodophenyl compounds, in which the radioisotope is bound by a sigma bond to the phenyl ring, may be prepared using the procedures described in EP 203,764, which generally involve substituting an organometallic group which is a tri-alkyl stannane of the formula Sn (R)$_3$ wherein R is a lower alkyl group, preferably Sn(n-Bu)$_3$ or SnMe$_3$, on a haloaromatic compound. A radioisotope of a halogen then is substituted for the organometallic group by halodemetalization.

"Ligand precursors" include, but are not limited to, these chelating compounds and molecules capable of binding radionuclides, prior to the radiolabeling step. Thus, the conjugates of the invention may comprise a chelating compound or the non-radiolabeled precursors of the above-described vinyl-iodo derivatives or para-iodophenyl compounds, attached to the linker.

Certain other types of therapeutic agents, such as cytotoxic drugs, may be used as ligands. In one embodiment of the invention, the ligand is a cytotoxic drug effective in eradicating cancer cells, and the targeting protein (e.g., a monoclonal antibody or fragment thereof) binds to the cancer cells. Examples of cytotoxic or antineoplastic drugs are methotrexate; pyrimidine analogs, such as fluorouracil and deoxyuridine; cytosine arabinoside, purine analogs, such as thioguanine, mercaptopurine and azathiopurine; vinca alkaloids, such as vincristine and vinblastine; actinomycin D; daunorubicin, doxorubicin, and other anthracycline derivatives; bleomycin; mitomycin; L-asparaginase; platinum derivatives, hydroxyurea; steroid hormones and alkalating agents, such as cyclophosphamide, cholorambucil, and nitrosourea derivatives.

The drugs suitable for use as a ligand are those which retain therapeutic activity when attached to a modified cellular substrate. The retention of therapeutic activity depends to a large degree on the chemical reaction procedures used to join the drug to a modified cellular substrate, and the position of the bond between the two moieties. The reaction procedures used to join the drug to the substrate will vary according to the chemical structure of the particular compounds to be joined, as described below. Any of a number of conventional cytotoxicity assays may be used to evaluate the cytotoxic activity of a particular drug-modified substrate conjugate, to identify those suitable for attachment to a targeting protein.

In addition, it is expected that the modified cellular substrate linkers will more effectively enhance the internalization and intracellular retention of therapeutic agents which are relatively small molecules (as opposed to larger therapeutic agents such as polypeptide toxins). It is believed that the target cell may be more likely to recognize the modified cellular substrate as a natural substrate to be internalized when the substrate linker is attached to a therapeutic agent which does not dwarf it.

The protein conjugates of the present invention may comprise more than one diagnostically or therapeutically effective agent. For example, a conjugate may comprise both a radionuclide and a cytotoxic drug. Conventional methods may be used to attach a radionuclide to a drug (See U.S. Pat. Nos. 4,620,971 and 4,485,086, which describe $^{111}In$-bleomycin and $^{111}In$- or $^{113}In$-porphyrin complexes, respectively). The radiolabeled drug then is attached to a modified cellular substrate linker which in turn is attached to a targeting protein to form a protein conjugate of the present invention.

The protein conjugate is designed to promote increased retention of the delivered ligand (i.e., a diagnostic or therapeutic agent or electron-dense material) within the target cells. Enhanced cellular retention is achieved by connecting the targeting protein to the ligand with a false biochemical substrate which also functions as the linking group of the protein conjugate. The linking group is recognized by the cell as a biochemical substrate, but the enzymes involved in its catabolism are not able to metabolize the linking group (substrate) due to its biochemical or chemical modification.

Thus, the modified substrate linker may play a role in enhancing internalization of the ligand bound thereto into target cells, since the cells may recognize the linker as a substrate which is normally taken into the cells. Once inside the cells, release of the ligand from the linker (which may increase the rate of export of the ligand from the cell) is minimized due to the modifications on the substrate which inhibit the enzymatic/metabolic degradation to which the corresponding unmodified substrates are subjected. The net result is enhanced cellular retention of the ligand. The enhancement of cellular retention is observed in vivo as a decrease in background radiation during diagnostic imaging and increased therapeutic effectiveness when the ligand comprises a therapeutic agent.

The linking group is a biochemical substrate, such as a sugar or a fatty acid; however, there are small replacement groups, such as side chains or insertions, that may be added to the substrate molecule to cause the linking group to become a false substrate. A given substrate may be modified by attaching or inserting one or more substituents. A preferred substitution to a linking group is the insertion of a tellurium atom into a fatty acid carbon chain. Silicon, with or without attached $C_{1-6}$ groups, may also be inserted within a fatty acid chain. Further, the fatty acid linking groups may be modified to contain one or more $C_{1-6}$ alkyl groups as branch points on the chain, or a phenyl group within the chain or as a branch group, to enhance retention of the protein conjugate within cells. Carbocyclic analogs of sugars (i.e., analogs in which the ring of the sugar unit contains only carbon atoms) also may be used. For example, a carbocyclic analog of ribose, wherein the oxygen atom in the ring is replaced by a carbon atom, may be used. Another example of a linking group is a halogenated (e.g., fluorinated) sugar derivative. Other naturally occurring sugar derivatives such as muramic acid, hyalobiuronic acid, and fucosamine are biochemically altered sugars which may be used as the modified substrate linker, or further derivatized to gain an additional enhancement of retention of ligands such as radionuclides and drugs within the target cells.

When the ligand is a chelated radionuclide, the retention of the non-metabolizable linking group/substrate is particularly valuable because release from a targeted cell prior to radionuclide decay degrades the quality of images (i.e., raises the background activity) in diagnostic or imaging applications, and increases the radiation dose to non-targeted areas in radiotherapy applications.

The methods by which the targeting protein and the ligand are attached to the modified cellular substrate linker to form a conjugate of the present invention will vary according to the chemical structures of the three components of a particular conjugate. Conventional chemical reaction procedures may be used, depending on such factors as the reactive functional groups present on a particular component. In some cases, a particular component may be derivatized to expose or attach reactive functional groups.

Many chelating compounds (as well as the radiohalogenated small molecules described above) comprise functional groups that will react with other compounds to bind the chelates thereto. Such functional groups include, but are not limited to, isothiocyanates, free amines, hydrazines, thiols, active esters (e.g., succinimidyl or 2,3,5,6-tetrafluorophenyl esters), and Michael acceptor groups (e.g., maleimides). Chelating compounds comprising functional groups suitable for reaction with a particular modified substrate linker (to bind the chelating compound to the linker) may be chosen for use.

Alternatively, appropriate chemical synthesis procedures may be employed to synthesize a ligand, or a precursor thereof, and a particular modified substrate as a single molecule, rather than synthesizing the two compounds separately and joining them afterward. For example, a modified fatty acid and a compound that will bind a radionuclide may be synthesized as a single molecule. One such ligand precursor to which a radionuclide will be attached is a compound comprising a phenyl ring having a tri-alkyl stannane substituted thereon in the para position, as shown in the examples below.

Likewise, the method for attaching the modified cellular substrate linker to a targeting protein such as an antibody will vary according to the chemical structure of the linker. Antibodies are proteins which contain a variety of functional groups; e.g., carboxylic acid (COOH) or free amine (—NH$_2$) groups, which are available for reaction with a suitable protein conjugation group on a linker molecule to bind the linker thereto. For example, a free amine on a lysine residue of an antibody will react with an active ester group on a linker to form an amide bond. Alternatively, the antibody and/or modified substrate may be derivatized to expose or attach additional reactive functional groups. The derivatization may involve attachment of any of a number of linker molecules such as those available from Pierce Chemical Company, Rockford, IL (See the Pierce 1986-87 General Catalog, pages 313-354).

Alternatively, derivatization may involve chemical treatment of the antibody; e.g., glycol cleavage of the sugar moiety of the glycoprotein antibody with periodate to generate free aldehyde groups. The free aldehyde groups on the antibody may be reacted with free amine or hydrazine groups on the modified cellular substrate linker to bind the linker thereto. (See U.S. Pat. No. 4,671,958.) Procedures for generation of free sulfhydryl groups on antibodies or antibody fragments also are known. (See U.S. Pat. No. 4,659,839.) The free sulfhydryl groups are reactive with maleimide groups which may be attached to the modified cellular substrate.

The bond between the targeting protein and the modified cellular substrate may be cleavable, if desired. The bond may be cleavable under conditions present at the target site (e.g., acidic pH, certain enzymatic activities, etc., depending on the characteristics of the particular target cells). A variety of linker molecules useful for joining two compounds through such cleavable bonds are known. Thus, once the targeting protein has served the purpose of delivering the conjugate to the target cells, the modified cellular substrate linker and ligand may be released therefrom. The bond between the modified cellular substrate linker and ligand should not be cleavable, since the linker is to remain attached to the ligand, at least for some time, to promote enhanced retention of the ligand in the target cells.

Thus, the modifications of the cellular substrates may additionally include attachment of functional groups reactive with a ligand or ligand precursor or a targeting protein. The substrate may be synthesized or derivatized using procedures that expose or attach such functional groups when the substrate does not naturally comprise suitable reactive groups. Alternatively, the modifications may additionally include attachment of a ligand precursor, as described above.

The protein conjugates prepared as described above are administered to a human or mammalian host in diagnostically or therapeutically effective amounts. The amounts will vary depending on such factors as the type of target cells and the antibodies used, since antibodies vary with respect to the number of receptors on the target cells and their affinity for the receptors. The dosage also will vary according to the agent used, as therapeutic agents such as drugs, for example, vary with respect to their potency.

Thus, the present invention also provides a method of eradicating target cells within a human or mammalian host, comprising administering to the host a protein conjugate of the invention, wherein the conjugate comprises a targeting protein that binds to the target cells; a chemically modified cellular substrate linker attached to the targeting protein; and a ligand attached to the linker, wherein the ligand comprises a therapeutic agent selected from the group consisting of cytotoxic drugs and therapeutically effective radionuclides.

When the ligand comprises a diagnostic agent, the present invention provides a method of detecting the presence of target cells within a human or mammalian host, comprising administering to the host a protein conjugate of the invention, wherein the conjugate comprises a targeting protein that binds to the target cells, and the ligand comprises a diagnostic imaging agent selected from the group consisting of diagnostic radioisotopes and electron dense chemicals; then detecting the biodistribution of the diagnostic imaging agent within the host. Conventional methods for detecting the biodistribution of the agent may be used, which will vary according to the particular diagnostic agent in the ligand. For example, the patient is scanned with a gamma camera to measure the biodistribution of the diagnostic radionuclide $^{99m}Tc$, after waiting a sufficient length of time to allow localization of the protein conjugate at the target site(s).

Whether the target cells are to be eradicated or detected, the targeting protein may be a monoclonal antibody or fragment thereof that binds to the target cells. An example of target cells is cancer cells.

The following examples are offered by way of illustration of the invention, and not by way of limitation. The compounds synthesized by the procedures of the following examples are represented in the Figures.

EXAMPLE I

Synthesis of a Modified Sugar Linking Group

The synthesis schemes described in Examples I through III are depicted in FIG. 1.

To a solution of 10 mg (0.02 mmole) of succinimidyl 4-(tri-n-butylstannyl)benzoate in 0.5 mL of acetonitrile is added 5.6 uL (4 mg, 0.04 mmole) of triethylamine followed by a solution of 5.0 mg (0.02 mmoles) of muramic acid (Sigma) in 0.15 mL of H$_2$O. The mixture is stirred at room temperature until complete as indicated by reverse phase HPLC, then partitioned between 1 mL of 5% aqueous HCl and 1 mL of diethyl ether. The ether layer is washed with brine, dried over magnesium sulfate, filtered and concentrated to yield 3-O-(1'-Carboxyethyl)-2-deoxy-2-((4-tri-n-butylstannyl)-benzamidyl)-D-glucose, compound 1 (shown in FIG. 1). Alternately, similar procedures may be used to produce compounds having other substituents of the formula —Sn(C$_{1-5}$ alkyl)$_3$ on the benzene ring at the para position.

The alcohol functionalities of compound 1 are protected using standard materials and methods to form compound 2.

To a solution of 0.02 mmole of compound 2 in 0.5 mL of THF is added 0.022 mmole of dicyclohexylcarbodiimide (Sigma) followed by 0.022 mmole of 2,3,5,6-tetrafluorophenol (Aldrich). The mixture is stirred at room temperature until complete as indicated by reverse phase HPLC. After quenching with 0.022 mmole of acetic acid, the mixture is concentrated and the residue is purified by chromatography on silica gel to yield hydroxyl protected 2-deoxy-3-0-(2,3,5,6-tetrafluorophenyl-1'-ethylcarboxylate)-2((4-tri-n-butylstannyl) benzamidyl)-D-glucose, compound 3. Compound 3 is a modified sugar linking group comprising a 2,3,5,6-tetrafluorophenyl protein conjugation group.

EXAMPLE II

Radiolabeling of a Modified Sugar Linking Group

Compound 3 is radioiodinated by adding approximately mately 10–50 ug (0.02–0.10 umole) compound 3 to 50 uL of 5% HOAc/methanol. Approximately 10–20 ug (0.08–0.15 umole) N-chlorosuccinimide in 10–20 uL methanol is added to the compound 3 solution. Next, 10 uL Na$^{125}$I solution (diluted in Delbecco's phosphate buffered saline; Gibco Labs) (100 uCi-2 mCi) is added. After 3–5 minutes at room temperature, 20 uL of a 0.25 ug/mL solution of Na$_2$S$_2$O$_5$ is added to stop the reaction. The reaction mixture is diluted with 50 uL PBS (phosphate buffered saline) solution, and a stream of N$_2$ is blown over the top of the solution until the volume is reduced to only an aqueous solution (approximately 80 uL). The radioiodinated compound 4 is deprotected (to compound 5) using standard procedures or under the basic conditions of the conjugation reaction used to form compound 6. Compounds 4 and/or 5 are radioiodinated modified sugar linking groups that can be used for protein labeling.

EXAMPLE III

Conjugating a Targeting Protein to a Radiolabeled Modified Sugar Linking Group

Compound 4 or 5 as a crude aqueous radioiodinated ester mixture is added to a vial containing buffered targeting protein solution (pH 8.5–9). The conjugation reaction is completed within 5 minutes at room temperature. The tetrafluorophenyl ester group of compound 4 reacts with a free amine group on a lysine residue of the protein to form an amide bond. A protein conjugate of the invention, compound 6, is thus prepared.

The conjugated targeting protein is purified from the non-conjugated radiolabeled modified sugar linking group using either a gel permeation chromatography column or a small pore filtration system (e.g., Centricon ultra centrifugation) to separate the protein conjugate from the unconjugated radioactivity.

EXAMPLE IV

Synthesis of a Modified Fatty Acid Linking Group

Figure 2:
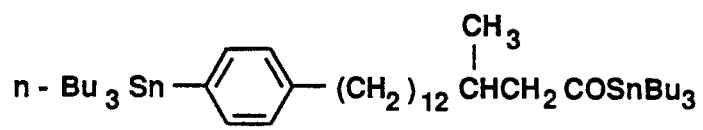
FIG. 2 depicts the intermediate compounds (7-10) in the synthesis of a protein conjugate of the invention comprising a modified fatty acid linker.
Figure 2:
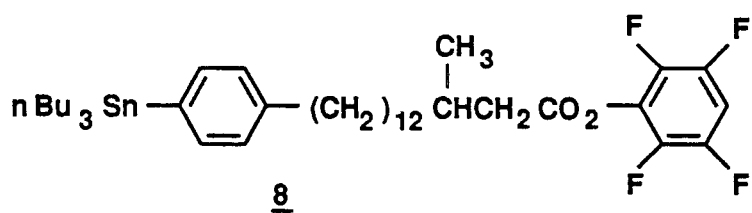
Figure 2:
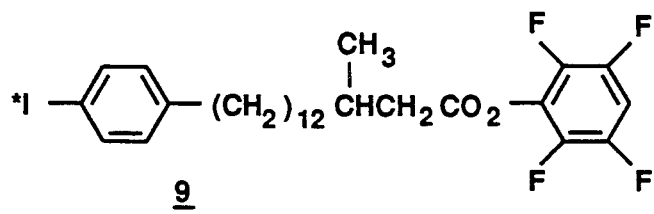
Figure 2:
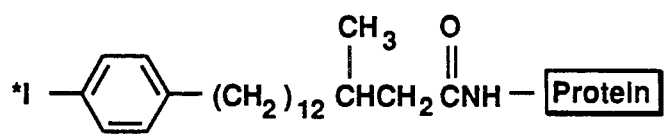

The synthesis schemes described in Examples IV through VI are depicted in FIG. 2.

To a −100° C. solution of 0.1 mmoles of 15-(4'-iodophenyl)-3-methylpentadecanoic acid (prepared according to the method of Knapp J. Org. Chem. 1984, 2322) in 5 mL of dry THF is added dropwise 0.21 mmoles of 1.6M n-butyllithium solution. After 15 minutes at −100° C., 0.21 mmoles of tri-n-butyltin chloride (Aldrich) is added over 15 minutes. The mixture is allowed to come to room temperature and stirred for 1 hour. Then 5 mL of saturated ammonium sulfate solution is added and the mixture is extracted with 10 mL of diethyl ether. The organic layer is washed with brine, dried (magnesium sulfate) and concentrated. The residue is purified by silica gel chromatography to yield tri-n-butylstannyl 3-methyl-15-(4'-tri-n- butylstannylphenyl) pentadecanoate, compound 7.

To a solution of 0.10 mmoles of compound 7 in 2.5 mL of dry THF was added 0.12 mmoles of dicyclohexylcarbodiimide (Sigma), followed by 0.12 mmoles 2,3,5,6 tetrafluorophenol (Aldrich). After the reaction was complete, the mixture was quenched with 0.12 mmoles of acetic acid and concentrated. Purification by silica gel chromatography yielded 2,3,5,6 tetrafluorophenyl 3-methyl-15-(4'-tri-n-butylstannylphenyl)-pentadecanoate, compound 8. Compound 8 is a modified fatty acid linking group comprising a tetrafluorophenyl ester protein conjugation group.

EXAMPLE V

Radiolabeling of a Modified Fatty Acid Linking Group

To a vial containing 10–50 ug (0.02–0.10 umole) compound 8 in 50 uL of 5% HOAc/methanol is added 10–20 ug (0.08–0.15 umole) N-chlorosuccinimide in 10–20 uL methanol. To this solution is added 10 uL $Na^{125}I$ solution (diluted in Delbecco's phosphate buffered saline; Gibco Labs) (100 uCi-2 mCi). After 3–5 minutes, 20 uL of a 0.25 g/mL solution of $Na_2S_2O_5$ is added. The reaction mixture is further diluted with 50 uL PBS solution, and a stream of $N_2$ was blown over the top of the solution until the volume is reduced to only aqueous solution (about 80 uL). The crude 2,3,5,6-tetrafluorophenyl-3-methyl-15(4'-iodophenyl)pentadecanoate, compound 9, is used directly for protein labeling. Compound 9 is a radiolabeled modified fatty acid linking group.

EXAMPLE VI

Conjugation of a Radiolabeled Modified Fatty Acid Linking Group to a Targeting Protein Compound 9 is transferred to a vial containing buffered protein solution (pH 8.5–9), or vice versa. The conjugation reaction occurs within 5 minutes at room temperature. The conjugated targeting protein, Compound 10, is purified from non-conjugated radioactivity using either a gel permeation chromatography column or a small pore filtration system (e.g., Centricon ultra centrifugation).

EXAMPLE VII

Synthesis of a Metallo Modified Fatty Acid Linking Group

Figure 3:
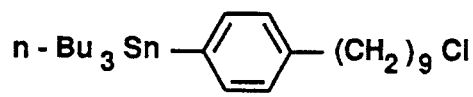
FIG. 3 depicts the intermediate compounds (11-16) in the synthesis of a protein conjugate of the invention comprising a modified fatty acid linker.
Figure 3:
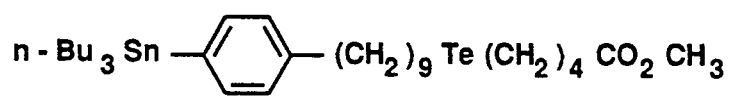
Figure 3:
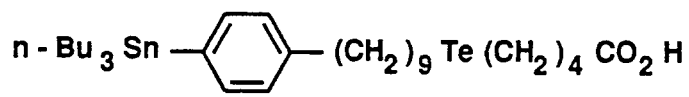
Figure 3:
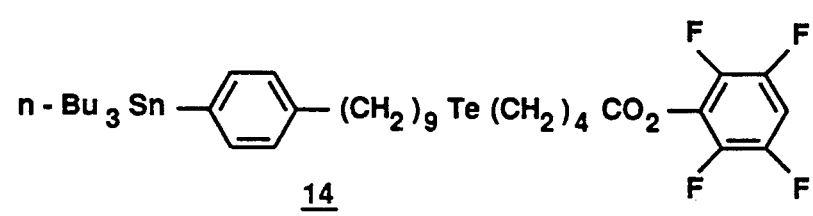
Figure 3:
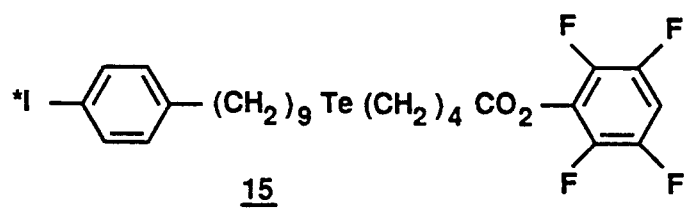
Figure 3:
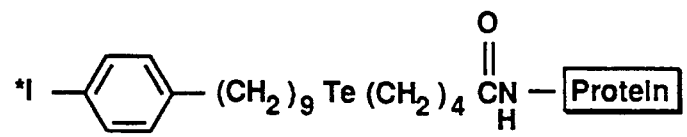

The synthesis schemes described in Examples VII through IX are depicted in FIG. 3.

To a −100° C. solution of 0.1 mmoles of 1-chloro-9-(4'-iodophenyl)nonane (prepared according to the method of Knapp, et al., *J. Nucl. Med.* 1982, 904) in 5 mL of dry THF is added 0.11 mmoles of 1.6M n-butyllithium solution. After 15 minutes at −100° C., the mixture is allowed to warm to room temperature and partitioned between 10 mL of saturated ammonium sulfate and 10 mL of diethyl ether. The organic layer is washed with brine, dried over magnesium sulfate and concentrated. The residue is purified by silica gel chromatography to yield 1-chloro-9-(4'-tri-n-butyl-stannylphenyl)-nonane, compound 11.

A solution of 0.1 mmole of bis-(methylvaleryl)ditelluride (prepared according to the method of Knapp et al., *J. Nucl. Med.* 1982, 904) in 5 mL of ethanol is reduced to the sodium salt by treatment with excess $NaBH_4$ in ethanol (5 mL). A solution of 0.2 mmoles of 1-chloro-9-(4'-tri-n-butylstannylphenyl)nonane is added dropwise and the mixture is refluxed under argon for 1 hr., cooled in an ice bath, diluted with water and extracted with ether. The ether extracts are washed with water, dried over magnesium sulfate and concentrated. The residue is purified by silica gel chromatography to yield methyl 15-(4'-tri-n-butylstannylphenyl)6-tellurapentadecanoate, compound 12.

A solution of 0.1 mmoles of compound 12 in 5 mL of THF is stirred with 0.2 mL of 1N NaOH. When the reaction is complete, 0.4 mL of 1N HCl is added and the mixture is partitioned between 10 mL of ether and 10 mL of water. The aqueous layer is extracted with ether and the combined extracts are washed with brine, dried over magnesium sulfate and concentrated to yield 15-(4'-tri-n-butylstannylphenyl)-6-tellurapentadecanoicacid, compound 13.

To a solution of 0.10 mmoles of compound 13 in 2.5 mL of dry THF is added 0.11 mmoles of dicyclohexylcarbodiimide (Sigma) followed by 0.11 mmoles of 2,3,5,6-tetrafluorophenol (Aldrich). When the reaction is completed, 0.11 mmoles of acetic acid is added and the mixture is concentrated. The residue is purified by silica gel chromatography to yield 2,3,5,6 tetrafluorophenyl 15-(4'-tri-n-butylstannylphenyl)-6-tellurapentadecanoate, compound 14. Compound 14 is a modified fatty acid linking group comprising a protein conjugation group.

EXAMPLE VIII

Radiolabeling of a Modified Fatty Acid

Compound 14 is radiolabeled with sodium $^{125}I$ by the procedure described in Example V to yield radiohalogenated compound 15.

EXAMPLE IX

Conjugating a Targeting Protein to a Radiolabeled Modified Fatty Acid Linking Group Radiohalogenated compound 15 is conjugated to a targeting protein using the procedure described in Example VI. The resulting protein conjugate is compound 16.

EXAMPLE X

Synthesis of a Modified Sugar Linking Group

Figure 4:
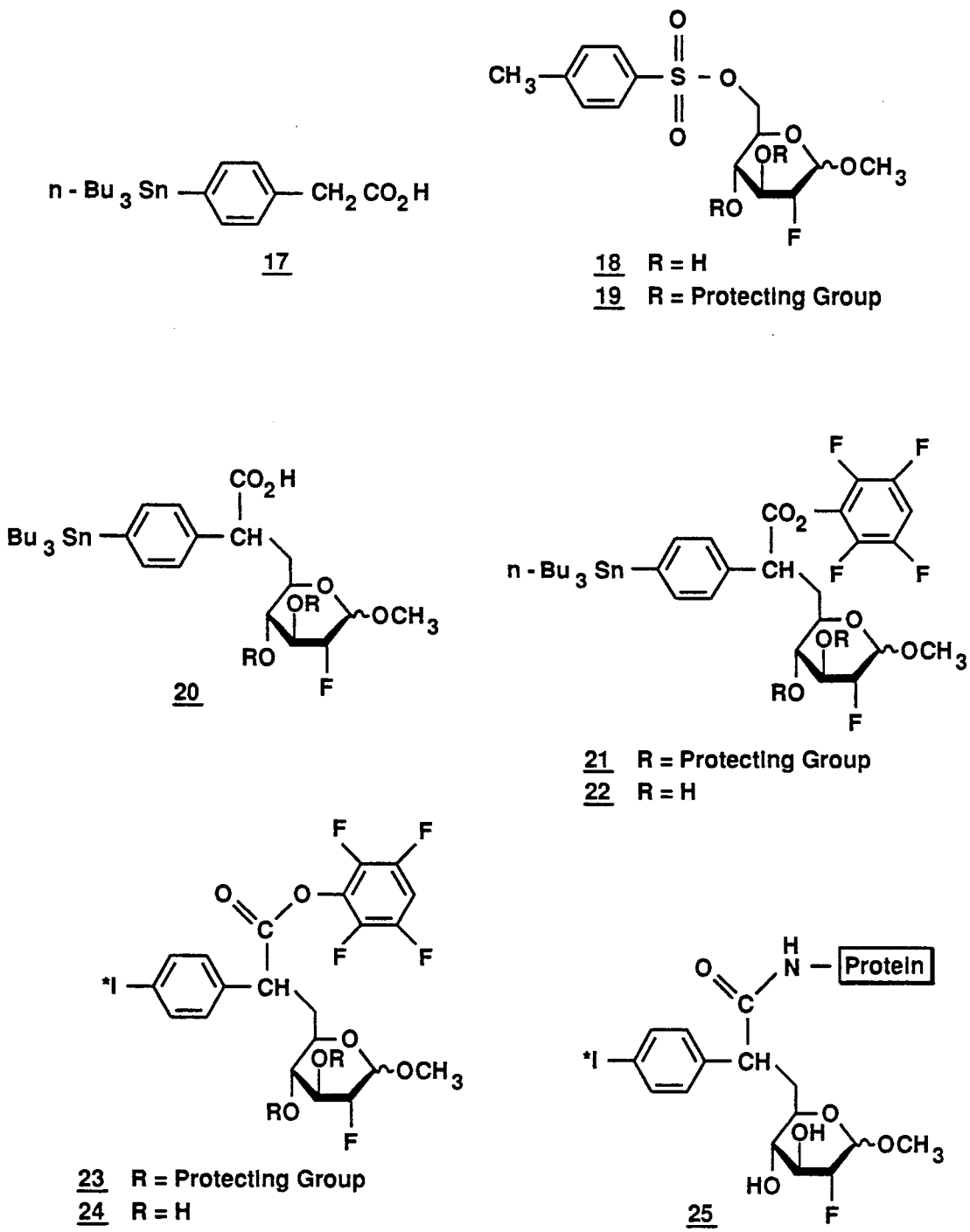
FIG. 4 depicts the intermediate compounds (17-25) in the synthesis of a protein conjugate of the invention comprising a modified sugar linker.

The synthesis schemes described in Examples X through XII are depicted in FIG. 4.

One equivalent of 4-bromophenylacetic acid (Aldrich) is dissolved in dry toluene and then added to 3 equivalents of hexabutylditin and 0.01 equivalents of tetrakis (triphenylphosphine)palladium. The solution is refluxed for 12 hours under $N_2$. The solvent is removed under reduced pressure. The residue is applied to a silica gel column and eluted with hexane to remove excess hexabutylditin. The product is isolated by elution with ethylacetate hexane mixtures. Removal of the solvents yields compound 17, p-tri-n-butylstannylphenyl acetic acid.

The compound, 2-deoxy-2-fluoro-D-glucose is synthesized using the procedure described in Tewson, *J. Org. Chem.*, 48, pp. 3507–10 (1983). The methyl ether is prepared by reacting 2-deoxy-2-fluoro-D-glucose with 1% HCl-Methanol using the general procedure as described in Hoffer *Chem. Ber.* 93, p. 2777 (1960). The methyl ether product is treated with p-toluenesulfonyl chloride (1 equivalent) in 10% pyridine-$CH_2Cl_2$ to yield the toluenesulfonate ester 2-deoxy-2-fluoro-6-p-toluenesulfonyl-D-glucose, compound 18. The hydroxyl functionalities are protected using the standard procedures and materials to yield compound 19.

Two equivalents of lithium diisopropylamine are added to compound 17 in dry THF. The solution is stirred at room temperature for 1 hour. Compound 19 in a THF solution (1 equivalent) is added dropwise to the solution of compound 17. After 30 min. H₂O is added followed by ethyl acetate. The organic phase is isolated, washed with H₂O, dried with anhydrous MgSO₄, and then the solvents are removed under reduced pressure. Compound 20, is purified by silica gel chromatography.

To a solution of compound 20 in THF is added 1 equivalent of dicyclohexylcarbodiimide (DCC) and 1.2 equivalents of tetrafluorophenol. The resultant mixture is allowed to stand at approximately 5° C. for 8 hours. The dicyclohexylurea (DCU) is filtered off. The THF is removed under reduced pressure and the tetrafluorophenyl ester product, compound 21, is chromatographed using a silica gel column and collected. The protecting group may be taken off using standard procedures to yield compound 22 or may be taken off after the radioiodination reaction.

EXAMPLE XI

Radioiodination of a Modified Sugar Linking Group

A 1.0 mg/mL solution of the tetrafluorophenyl ester, (compound 21 or 22) is prepared in 1% HOAc-MeOH. Fifty uL of the solution is added to 10 uL of a NCS solution (1.0 mg/mL in methanol) and 10 uL of phosphate buffered saline. 1-10 uL of $Na^{125}I$ solution is added to the mixture. The mixture is kept at room temperature for approximately 15 minutes. The reaction is quenched with 10 uL $NaHSO_3$ (0.72 mg/mL in H₂O). The radioiodinated modified sugar linker group, (compound 23 or 24) is used for protein labeling.

EXAMPLE XII

Conjugating the Radioiodinated Modified Sugar Linking Group to a Targeting Protein The radioiodination reaction mixture of Example XI is evaporated to near dryness under a gentle stream of nitrogen A targeting protein solution in pH 8.5-9.5 buffer is added to the radioiodinated modified sugar linking group (compound 23 or 24) or vice versa. The conjugation mixture is shaken gently, and, after 5 minutes, applied to a size exclusion gel column and eluted with phosphate buffered saline. The protein conjugate, compound 25, is thereby isolated.

What is claimed is:

1. A conjugate of the formula:

Y—Linker—Ligand wherein:
Y represents a targeting protein;
Linker represents a fluorinated analog of a naturally occurring sugar substrate, wherein the sugar substrate comprises at least one five-, six-, or seven-membered heterocyclic ring bearing multiple hydroxyl groups and having oxygen as the heteroatom, and wherein the fluorinated analog of said sugar substrate comprises one or two fluorine atoms bonded to a carbon atom of the heterocyclic ring; and
Ligand represents a ligand that comprises a diagnostic or therapeutic agent.

2. The conjugate of claim 1 wherein said linker is a polysaccharide of from 2 to about 10 saccharide units, comprising at least one saccharide unit which is the fluorinated analog of a naturally-occurring sugar substrate.

3. The conjugate of claim 1 wherein said ligand comprises a diagnostic or therapeutic agent selected from the group consisting of radionuclides, cytotoxic drugs, and diagnostic imaging agents.

4. The conjugate of claim 3 wherein said ligand comprises a radionuclide bound by a sigma bond or a radionuclide metal chelate.

5. The conjugate of claim 1 wherein said targeting protein is selected from the group consisting of antibodies, antibody fragments, hormones, and serum proteins.

6. The conjugate of claim 5 wherein the targeting protein is a monoclonal antibody or a monoclonal antibody fragment.

7. The conjugate of claim 6 wherein the monoclonal antibody or fragment thereof binds to cancer cells.

8. A conjugate of the formula:

Y—Linker—Ligand wherein:
Y represents a targeting protein;
Linker comprises fluorinated deoxyglucose; and
Ligand represents a ligand that comprises a diagnostic or therapeutic agent.

9. The conjugate of claim 8, wherein Linker comprises 2-deoxy-2-fluoro-D-glucose.

10. A conjugate of the formula:

Y—Linker—Ligand wherein:
Y represents a targeting protein or a protein conjugation group;
Linker represents a fluorinated analog of a naturally occurring sugar substrate, wherein the sugar substrate comprises at least one five-, six-, or seven-membered heterocyclic ring bearing multiple hydroxyl groups and having oxygen as the heteroatom, and wherein the fluorinated analog of said sugar substrate comprises one or two fluorine atoms bonded to a carbon atom of the heterocyclic ring; and
Ligand represents a ligand comprising a radionuclide metal bound within a chelating compound selected from $N_2S_2$, $N_3S$, and $N_4$ chelating compounds.

11. A conjugate of the formula:

Y—Linker—Ligand wherein:
Y represents a targeting protein or a protein conjugation group;
Linker represents a fluorinated analog of a naturally occurring sugar substrate, wherein the sugar substrate comprises at least one five-, six-, or seven-membered heterocyclic ring bearing multiple hydroxyl groups and having oxygen as the heteroatom, and wherein the fluorinated analog of said sugar substrate comprises one or two fluorine atoms bonded to a carbon atom of the heterocyclic ring; and
Ligand represents a ligand comprising a radiolabeled molecule that comprises the chemical structure:

wherein X* represents a radiohalogen.

12. The conjugate of claim 10 or 11 wherein said targeting protein is a monoclonal antibody or monoclonal antibody fragment.

* * * * *

UNITED STATES PATENT AND TRADEMARK OFFICE
CERTIFICATE OF CORRECTION

PATENT NO. : 5,057,301

DATED : October 15, 1991

INVENTOR(S) : Wilbur et al.

It is certified that error appears in the above-indentified patent and that said Letters Patent is hereby corrected as shown below:

On the title page: Item

[75] Inventors: Please delete the semicolon after "Edmonds" and insert a comma therefor, and delete "Mark Hylarides, Everett, both of"

Signed and Sealed this

Twenty-first Day of November, 1995

Attest:

BRUCE LEHMAN

Attesting Officer

Commissioner of Patents and Trademarks